United States Patent [19]

Mochida et al.

[11] Patent Number: 4,760,060
[45] Date of Patent: Jul. 26, 1988

[54] 3-HETEROARALKYLTHIO CARBACEPHEM COMPOUNDS AND ANTIBACTERIAL PHARMACEUTICAL COMPOSITION

[75] Inventors: Kenichi Mochida, Hiratsuka; Takehiro Ogasa, Machida; Junichi Shimada, Machida; Tadahi Hirata, Yokohama; Kiyoshi Sato, Mishima; Ryo Okachi, Chiba, all of Japan

[73] Assignee: Kyowa Hakko Kogyo Co., Ltd., Tokyo, Japan

[21] Appl. No.: 798,320

[22] Filed: Nov. 15, 1985

[30] Foreign Application Priority Data

Nov. 15, 1984 [JP] Japan .................... 59-241380

[51] Int. Cl.$^4$ .................... A61K 43/40; C07D 487/06; C07D 501/14
[52] U.S. Cl. .................... 514/210; 514/183; 514/184; 514/186; 514/200; 514/202; 514/203; 514/204; 514/208; 540/205; 540/215
[58] Field of Search .............. 546/183; 514/299, 184, 514/186, 200, 202, 203, 204, 210, 208, 183; 540/205

[56] References Cited

U.S. PATENT DOCUMENTS

| | | | |
|---|---|---|---|
| 4,123,528 | 10/1978 | Cama et al. | 546/183 |
| 4,150,156 | 4/1979 | Beattie | 540/215 |
| 4,226,866 | 10/1980 | Christensen et al. | 546/183 |
| 4,256,739 | 3/1981 | Woodward et al. | 424/200 |
| 4,278,793 | 7/1981 | Dürckheimer et al. | 546/183 |

FOREIGN PATENT DOCUMENTS

| | | |
|---|---|---|
| 0025017 | 11/1981 | European Pat. Off. . |
| 0133678 | 6/1985 | European Pat. Off. . |
| 2041923 | 9/1980 | United Kingdom . |

OTHER PUBLICATIONS

Helv. Chim. Acta., vol. 57, No. 7 (1975) 208:9.
J. Am. Chem. Soc., vol. 96, No. 15 (1974) 4986:7.
Chem. Pharm. Bull., vol. 28, No. 5 (1980) 1563:77.
Hirata et al., CA93-239247t.

Primary Examiner—Donald G. Daus
Assistant Examiner—Cecilia Shen
Attorney, Agent, or Firm—Fitzpatrick, Cella, Harper & Scinto

[57] ABSTRACT

Carbacephem and cephem compounds represented by the formula:

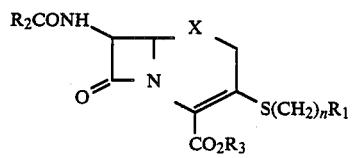

[Wherein X is S or $CH_2$; n is an integer of 1 to 5; $R_1$ is an unsubstituted or substituted heterocyclic group (where the heterocyclic group is a 5- or 6-membered heterocyclic group having 1 to 4 of O, S and N); $R_2$ is a group represented by the formula:

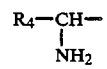

(where $R_4$ is an unsubstituted or substituted phenyl or 2-aminothiazolyl) or a group represented by the formula:

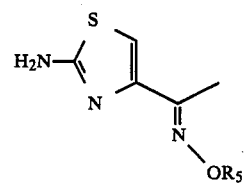

(where $R_5$ is an unsubstituted or substituted lower alkyl); $R_3$ is hydrogen, an alkali metal, an alkaline earth metal, an organic ammonium group or an ester residue, and $R_1$ may be a quaternary ammonium group, where $—CO_2R_3$ represents $—CO_2^-$] have strong antibacterial activity against Gram-positive and Gram-negative bacteria, and are useful for treating various infections.

2 Claims, No Drawings

3-HETEROARALKYLTHIO CARBACEPHEM COMPOUNDS AND ANTIBACTERIAL PHARMACEUTICAL COMPOSITION

BACKGROUND OF THE INVENTION

This invention relates to carbacephem and cephem compounds having an antibacterial activity and a substituted thio group at the 3-position, and pharmaceutical compositions containing the same.

Many patent applications have so far been field for cephem or carbacephem compounds, among which ceftizoxime, cefmenoxime, ceftriaxone, etc. are known as those having a heterocyclic thio group at the 3-position. As a cephem compound having a heterocyclic thio group at the 3-position, a compound represented by the formula:

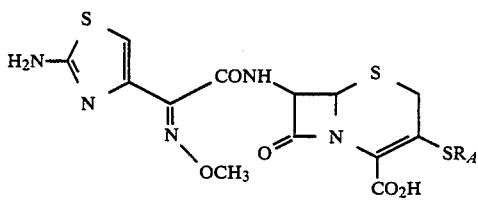

(wherein $R_A$ is a heterocyclic group) is disclosed in Japanese Published Unexamined patent application Ser. No. 38392/1980, which corresponds to EP 9008-A, and a compound represented by the formula:

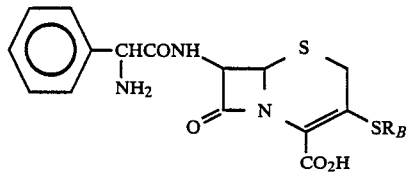

(wherein $R_B$ is a heterocyclic group) is disclosed in Japanese Published Unexamined patent application Ser. No. 83492/1977, which corresponds to U.S. Pat. No. 4,256,739. As to a carbacephem compound, a patent application was filed for a compound represented by the formula:

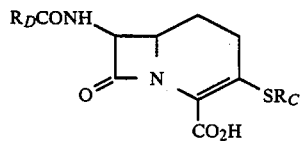

(wherein $R_C$ and $R_D$ have the same meanings as $R_1$ and $R_2$ defined hereinafter, respectively) by the present applicant (U.S. patent application Ser. No. 702,623 filed on Feb. 19, 1985, U.S. Pat. No. 4,640,919).

Antibiotics having wide antibacterial spectrum and strong antibacterial activity are always in demand.

DETAILED DESCRIPTION OF THE INVENTION

The present invention relates to carbacephem and cephem compounds represented by the formula (I):

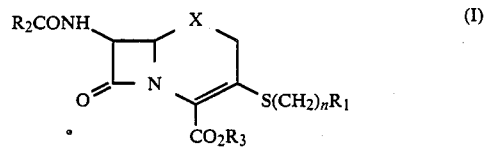

(wherein X is S or $CH_2$; n is an integer of 1 to 5; $R_1$ is an unsubstituted or substituted heterocyclic group (where the heterocyclic group is a 5- or 6- membered heterocyclic group having 1 to 4 of O,S and N); $R_2$ is a group represented by the formula:

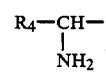

(wherein $R_4$ is an unsubstituted or substituted phenyl or 2-aminothiazolyl), or a group represented by the formula:

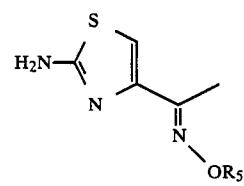

(wherein $R_5$ is an unsubstituted or substituted lower alkyl group); $R_3$ is hydrogen, an alkali metal, an alkaline earth metal, an organic ammonium group or an ester residue, and $R_1$ may be a quaternary ammonium group, where $-CO_2R_3$ represents $-CO_2-$] the compounds are hereinafter referred to as Compound (I), and compounds of other formula numbers are likewise referred to], and further to a pharmaceutical composition containing a Compound (I) as an active ingredient.

The compound (I) has a strong antibacterial activity on not only the Gram-negative bacteria, but also gram-positive bacteria.

In the definition of $R_1$, the preferable heterocyclic group is a 5- or 6- membered monoheterocyclic group having only 1 to 4N heteroatoms and the largest number of non-cumulative double bonds, a 5- and 6- membered monoheterocyclic group having only one S or O heteroatom and the largest number of non-cumulative double bonds, or a 5- or 6- membered monoheterocyclic group having one S or O heteroatom and one or two N heteroatoms and the largest number of non-cumulative double bonds. More specifically, the preferable heterocyclic group includes, for example, pyridyl, tetrazolyl, thiazolyl, thiadiazolyl, oxazolyl, triazolyl, pyrimidyl, imidazolyl, triazinyl, etc. The substituent on the heterocyclic group includes straight or branched lower alkyls having 1 to 6 carbon atoms (methyl, ethyl, etc.), hydroxyl, amino, nitro, $-(CH_2)_mY$ (where Y represents hydroxyl, carboxyl, carbamoyl, or sulfo, and m represents an integer of 1 to 5), etc.

When the substituent is a lower alkyl or $-(CH_2)_mY'$ bonded to N on the heterocyclic group (where $Y'$ is hydroxyl, carboxyl, or carbamoyl, and m has the same meaning as defined above), $R_1$ can be a quaternary ammonium group. In that case, the counter ions can be exemplified by $-CO_2-$ as ionized group of $-CO_2R_3$, etc.

In the definition of $R_4$, the substituent on the phenyl group includes straight or branched lower alkyls having 1 to 6 carbon atoms, hydroxyl, amino, nitro, carboxyl, etc. In the definition of $R_5$, the lower alkyl includes straight or branched lower alkyls having 1 to 7 carbon atoms (methyl, ethyl, etc.) and the substituent includes hydroxyl, carboxyl, sulfo, etc.

In the definition of $R_3$, the alkali metal includes sodium, potassium, etc., the alkaline earth metal includes calcium, magnesium, etc., and the organic ammonium group includes ammonium groups of organic amines such as basic amino acids. In the definition of $R_3$, the ester residue represents groups that are relatively easily releasable in vivo, as represented by the formula:

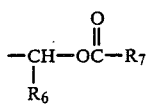

(where $R_6$ is hydrogen or a lower alkyl having 1 to 6 carbon atoms, and $R_7$ is a lower alkyl having 1 to 6 carbon atoms or phenyl), or by the formula:

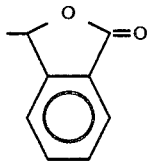

The process for preparing the compound (I) is described below:

The compound (I) where $R_3$ is hydrogen [which is hereinafter referred to as compound (I-1)] can be prepared by subjecting a compound represented by the formula (II):

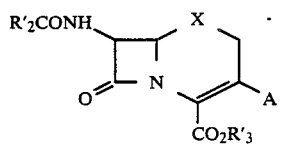

[where $R'_2$ represents $R_2$ or $R_2$ whose amino group is protected by an amino protective group; $R'_3$ represents a carboxyl protective group; A represents chlorine or a group represented by the formula $-OSO_2R_8$ [where $R_8$ is a lower alkyl having 1 to 6 carbon atoms (for example, methyl) or an unsubstituted or substituted aryl group having 6 to 20 carbon atoms (for example, phenyl, naphthyl, tolyl, etc.)]; X has the same meaning as defined above] to reaction with a thiol represented by the formula $HS(CH_2)_nR_1$ (where $R_1$ and n have the same meanings as defined above) in the presence of a base in an inert solvent, and, if necessary, by releasing the protective group therefrom. The process for preparing the compound (II) is disclosed in Japanese Published Unexamined patent application Ser. No. 16491/1981, which corresponds to U.S. Pat. No. 4,708,956 and U.S. patent application Ser. No. 702,623 or shown in Reference Examples.

Any amino protective group can be used as $R'_2$ in the general formula (II), so long as it is an easily releasable amino protective group as used in the peptide chemistry, and particularly it is exemplified by trityl, formyl, chloroacetyl, bromoacetyl, 2,2,2-trichloroacetyl, t-butoxycarbonyl, benzyloxycarbonyl, etc. Any carboxyl protective group can be used as $R'_3$, so far as it is an easily releasable protective group as used in the peptide chemistry, and particularly it is exemplified by t-butyl, benzyl, p-nitrobenzyl, benzhydryl, trityl, trimethylsilyl, etc.

The inert solvent to be used in the reaction of the compound (II) with thiol includes dimethylformamide, dimethylsulfoxide, tetrahydrofuran, chloroform, methylene chloride, acetonitrile, etc. As a base, a metal hydride such as sodium hydride, lithium hydride, etc., an organic amine such as triethylamine, N,N-diisopropylethylamine, N-methylmorpholine, etc., can be used. The reaction is carried out at 0° to 90° C., and it is preferable to use 1 to 4 equivalent weights of thiol on the basis of the compound (II) and also it is preferable to use an equivalent weight of the base on the basis of thiol. The thus obtained product is subjected to the successive removal of protective group as such or after purification according to silica gel column chromatography, etc. A compound (I) where $R_1$ is a quaternary ammonium group can also be prepared according to another procedure, i.e. by subjecting a compound (II) to reaction with a thiol represented by $R'_1(CH_2)_nSH$ (where $R'_1$ represents $R_1$ other than the quaternary ammonium group and n has the same meaning as defined above) in the same manner as described above, and by converting the product to a quaternary ammonium salt according to the conventional procedure using a compound represented by the formula $R_9Z$ [where $R_9$ is a straight or branched lower alkyl having 1 to 6 carbon atoms (methyl, ethyl, etc.) or a group represented by the formula $-(CH_2)_mY'$ (where $Y'$ is hydroxyl, carboxyl or carbamoyl, and m has the same meaning as defined above), and Z is a halogen such as chlorine, bromine, iodine, etc., or methanesulfonyloxy, p-toluenesulfonyloxy, trifluoromethanesulfonyloxy, etc.], and, if necessary, by releasing the protective group.

The removal of the protective group can be carried out according to the procedure frequently used in the cephalosporin chemistry without deteriorating the functional groups of the compound. For example, conversion to carboxyl group can be attained with trifluoroacetic acid, formic acid, etc. when $R'_3$ is t-butyl or benzhydryl, or by catalytic reduction when $R'_3$ is p-nitrobenzyl or benzhydryl. When the protective group in $R'_2$ is t-butoxycarbonyl, it can be removed with trifluoroacetic acid or formic acid, and in the case of trityl, it can be removed by acetic acid or hydrochloric acid. In the case of benzyloxycarbonyl, it can be removed by catalytic reduction. However, a combination of releasing the carboxyl protective group and the amino protective group at the same time is desirable.

The thus obtained compound (I-1) is, if necessary, subjected to reaction with various inorganic and organic bases or to esterification, according to the conventional procedure, whereby the compound (I) having $R_3$ other than hydrogen can be derived.

The compound (I) has a strong antibacterial effect on the gram-positive bacteria and the gram-negative bacteria, whereas its toxicity is very low. For example, $LD_{50}$ values of the compounds obtained in the following Examples 2, 9 and 11 by intravenous administration against mouse are 1.8 g/kg, 1.8 g/kg and more than 2.5 g/kg, respectively. Thus, the compound (I) is useful for treatment of various infections, as a sterilizer and as an antiseptic component.

Thus, the invention includes within its scope pharmaceutical compositions comprising, as an active ingredient, a Compound (I) in association with a pharmaceutical carrier or diluent. The compounds of this invention are administered by parenteral (intramuscular, intraperitoneal, intravenous or subcutaneous injection routes), oral or rectal route of administration and can be formulated in dosage forms appropriate for each route of administration.

Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions or by heating the compositions. They can also be manufactured in the form of sterile solid compositions which can be dissolved in sterile water or some other sterile injectable medium immediately before use.

Compositions for oral administration may be presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth or polyvinyl-pyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agent such as sodium lauryl sulfate. The tablets may be coated according to methods well known in the art. Oral liquid preparations may be in the form of aqueous or oily suspension, solution, emulsions, syrups, etc., or may be presented as a dry product, for reconstitution with water or other suitable vehicle before use. Such liquid preparations may contain conventional additive such as suspending agents, for example, sorbitol syrup, methyl cellulose, glucose sugar syrup, gelatin, hydroxyethylcellulose, carboxymethylcellulose, aluminum stearate gel, emulsifying agents, for example, lecithin or sorbitan monooleate; non-aqueous vehicles, which may include edible oils, for example, almond oil, coconut oil, propylene glycol or ethyl alcohol; preservatives, for example, methyl or propyl p-hydroxybenzoates or sorbic acid.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 and 350 mg/kg of body weight daily are administered to mammalian patients to achieve an antibiotic effect.

The present invention is further described below, referring to Examples and Reference Examples.

EXAMPLE 1

Preparation of (6R, 7S)-7-[2-(2-aminothiazol-4-yl)-2-syn-methoxyiminoacetamido]-3-(4-pyridyl) methylthio-1-azabicyclo [4.2.0]-oct-2-en-8-oxo-2-carboxylic acid At first, 439 mg of benzhydryl ester of (6R, 7S)-7-[2-(2-tritylaminothiazol-4-yl)-2-syn-methoxyiminoacetamido]-3-methanesulfonyloxy-1-azabicyclo[4.2.0]-oct-2-en-8-oxo-2-carboxylic acid was dissolved in 4 ml of dimenthylformamide (DMF), and 0.13 ml of 4-mercaptomethylpyridine and 0.156 ml of diisopropylethylamine were added thereto at room temperature. The mixture was subjected to reaction for 2 hours. The reaction mixture was concentrated under reduced pressure, and 50 ml of ethyl acetate and 50 ml of water were added to the residue. The organic layer was separated therefrom, and the solvent was removed therefrom by distillation under reduced pressure. The thus obtained oily matter was purified by column chromatography using 25 ml of silica gel (eluting agent: ethyl acetate), whereby 422 mg of benzhydryl ester of (6R, 7S)-7-[2-(2-tritylaminothiazol-4-yl)-2-syn-methoxyiminoacetamido]-3-(4-pyridyl) methylthio-1-azabicyclo [4.2.0]-oct-2-en-8-oxo-2-carboxylic acid was obtained as a light yellow powder (yield: 93%). Then, 200 mg of the powder was dissolved in 2 ml of methylene chloride and 0.2ml of anisole, and 2 ml of trifluoroacetic acid was added thereto. The mixture was subjected to reaction at room temperature for one hour. The reaction mixture was concentrated under reduced pressure, and the residue was dissolved in 4 ml of methanol and 0.4 ml of water, and the solution was left standing at room temperature for 2 hours. The reaction solution was concentrated under reduced pressure, and the residue was purified by column chromatography using 40 ml of Diaion HP-10 (adsorption resin manufactured by Mitsubishi Chemical Industries Ltd., Japan) (eluting agent; water:methanol=2:1.Eluting agent having the same composition as described here was used with respect to Diaion HP-10 in the following examples.), whereby 75 mg of a white powder was obtained. The powder had the following physical properties and was identified to be the captioned compound.

Yield: 65.4%.

IR $\nu$ max KBr(cm$^{-1}$) 1737, 1696, 1655, 1638, 1611, 1560, 1541, 1503

NMR(DMSO-d$_6$) $\delta$ 9.26(1H, d), 8.53(2H, d), 7.38(2H, d), 7.33(2H, s), 6.76(1H, s), 5.20(1H, dd), 4.10(2H, s), 3.96(3H, s)

EXAMPLE 2

Preparation of (6R, 7S)-7-[2-(2-aminothiazol-4-yl)-2-synmethoxyiminoacetamido]-3-(1-methylpyridinium-4-yl)methylthio-1-azabicyclo [4.2.0]-oct-2-en-8-oxo-2-carboxylate At first, 198 mg of benzhydryl ester of (6R, 7S)-7-[2-(2-tritylaminothiazol-4-yl)-2-syn-methoxyiminoacetamido]-3-(4-pyridyl)methylthio-1-azabicyclo[4.2.0]-oct-2-en-8-oxo-2-carboxylilc acid obtained in the same manner as in Example 1 was dissolved in 5 ml of chloroform, and one ml of methyl iodide was added thereto. The mixture was subjected to reaction at room temperature overnight. The reaction mixture was concentrated, and 2 ml of methylene chloride, 0.2 ml of anisole and 2 ml of trifluoroacetic acid were added to the residue. The mixture was subjected to reaction at room temperature for 2 hours. The reaction mixture was concentrated under reduced pressure, and 4 ml of methanol and 0.4 ml of water were added to the residue. After having been adjusted to pH 1.0, the mixture was left standing at room temperature for 2 hours. The solvent was removed from the reaction mixture by distillation, and the residue was purified by column chromatography using 50 ml of Diaion HP-10, whereby 82 mg of a yellow powder was obtained.

The powder had the following physical properties and was identified to be the captioned compound.

Yield: 68.2%.

IR $\nu$ max KBr(cm$^{-1}$) 1749, 1646, 1559, 1541, 1469

EXAMPLE 3

Preparation of (6R, 7S)-7-[2-(2-aminothiazol-4-yl)-2-syn-methoxyimino-acetamido]-3-(2-pyridyl)methylthio-1-azabicyclo [4.2.0]-oct-2-en-8-oxo-2-carboxylic acid The same procedure as in Example 1 was repeated except that 2- mercaptomethylpyridine was used in place of the 4-mercaptomethylpyridine used in Example 1, whereby 68 mg of a white powder was obtained. The powder had the following physical properties and was identified to be the captioned compound.

Yield: 59.3%

IR $\nu$ max KBr(cm$^{-1}$) 1747, 1653, 1541, 1508, 1465, 1434

NMR(DMSO-d$_6$) $\delta$ 9.28(1H, d), 8.48(1H, m), 7.85(1H, dt), 7.4–7.2(2H, m), 7.20(2H, s), 6.77(1H, s), 5.40(1H, dd), 4.19(2H, s), 3.84(3h, s)

EXAMPLE 4

Preparation of (6R, 7S)-7-[2-(2-aminothiazol-4-yl)-2-syn-methoxyimino-acetamido]-3-(3-pyridyl)methylthio-1-azabicyclo [4.2.0]-oct-2-en-8-oxo-2-carboxylic acid The same procedure as in Example 1 was repeated except that 3-mercaptomethylpyridine was used in place of the 4-mercaptomethylpyridine used in Example 1, whereby 62 mg of a white powder was obtained. The powder had the following physical properties and was identified to be the captioned compound.

Yield: 54%.

IR $\nu$ max KBr(cm$^{-1}$) 1745, 1683, 1654, 1543, 1539

NMR(DMSO-d$_6$) $\delta$ 9.23(1H, d), 8.52(H, m), 7.6–7.8(1H, m), 7.14–7.24(2H, m), 7.10(2H, s), 6.77(1H, s), 5.2(1H, dd), 4.13(2H, s), 3.97(3H, s)

EXAMPLE 5

Preparation of (6R, 7S)-7-[(R) phenylglycylamido]-3-(1-methylpyridinium-4-yl)methylthio-1-azabicyclo[4 2.0]-oct-2-en-8-oxo-2-carboxylate At first, 616 mg of benzhydryl ester of (6R, 7S)-7-[(R)-N-t-butoxycarbonylphenylglycylamido]-3-chloro-1-azabicyclo [4.2.0]-oct-2-en-8-oxo-2-carboxylic acid was dissolved in 5 ml of DMF, and 0.24 ml of 4-mercaptomethylpyridine and 0.26 ml of diisopropylethylamine were added thereto. The mixture was stirred at room temperature for one hour. The reaction mixture was concentrated under reduced pressure. Then, 50 ml of ethyl acetate and 50 ml of water were added to the residue, and the organic layer was separated therefrom. The organic layer was washed with water, and the solvent was removed therefrom by distillation. Then, 10 ml of methylene chloride and 1 ml of methyl iodide were added to the residue, and the mixture was stirred overnight. The reaction mixture was concentrated, and 5 ml of methylene chloride, 0.5 ml of anisole and 5 ml of trifluoroacetic acid were added to the residue. The mixture was subjected to reaction at room temperature for one hour. The reaction mixture was concentrated, and the resulting light yellow oily matter was dissolved in water. The solution was purified by column chromatography using 50 ml of Diaion HP-10, whereby 213 mg of a light yellow powder was obtained. The powder had the following physical properties and was identified to be the captioned compound.

Yield: 47%

IR $\nu$ max KBr(cm$^{-1}$) 1749, 1696, 1683, 1652, 1647, 1599, 1547, 1537

NMR (D$_2$O) $\delta$ 8.65(2H, d), 7.91(2H, d), 7.43(5H, s), 5.30(1H, d), 5.23(1H, s), 4.38(3H, s), 4.20(2H, s), 3.8(1H, m), 2.5–2.2(2H, m), 1.8–1.0(2H, m)

EXAMPLE 6

Preparation of (6R, 7S)-7-[2-(2-aminothiazol-4-yl)-2-syn-methoxyimino-acetamido]-3-[(2-methylthiazol-4-yl) methylthio]-1-azabicyclo [4.2.0]-oct-2-en-8-oxo-2-carboxylic acid The same procedure as in Example 1 was repeated, except that 0.15 ml of 4-mercaptomethyl-2-methyl-thiazol was used in place of 0.13 ml of the 4-mercaptomethylpyridine used in Example 1, whereby 74 mg of a white powder was obtained. The powder had the following physical properties and was identified to be the captioned compound.

Yield 65%

IR $\nu$ max KBr(cm$^{-1}$) 1749, 1664, 1528, 1508, 1458

NMR(CD$_3$OD) $\delta$ 7.20(1H, s), 6.79(1H, s), 5.43(1H, d), 4.13(2H, s), 3.98(3H, s), 3.8(1H, m), 2.63(3H, s)

EXAMPLE 7

Preparation of (6R, 7S)-7-[2-(2-aminothiazol-4-yl)-2-syn-methoxyimino-acetamido]-3-[2-(1-methylpyridinium-4-yl) ethylthio]-1-azabicyclo [4.2.0]-oct-2-en-8-oxo-2-carboxylate At first, 434 mg of benzhydryl ester of (6R, 7S)-7-[2-(2-tritylaminothiazol-4-yl)-2-syn-methoxyimino-acetamido]-3-methanesulfonyloxy-1-azabicyclo [4.2.0]-oct-2-en-8-oxo-2-carboxylic acid was dissolved in 5 ml of DMF, and 1.6 ml of 4-mercaptoethylpyridine and 2.4 ml of diisopropylethylamine were added thereto. The mixture was subjected to reaction at room temperature for 1.5 hours. The reaction mixture was concentrated under reduced pressure and 50 ml of ethyl acetate and 50 ml of water were added to the residue. The organic layer was separated therefrom, and the solvent was removed from the organic layer by distillation. Then, 10 ml of methylene chloride and 1 ml of methyl iodide were added to the residue, and the mixture was subjected to reaction at room temperature for 18 hours. The solvent was removed from the reaction mixture by distillation, and 5 ml of methylene chloride, 0.5 ml of anisole and 5 ml of trifluoroacetic acid were added to the resulting light brown solid. The mixture was stirred at room temperature for 2 hours. The reaction mixture was concentrated, and the residue was dissolved in a small amount of water. The solution was purified by column chromatography using Diaion HP-10, whereby 92 mg of a light brown powder was obtained. The powder had the following physical properties and was identified to be the captioned compound.

Yield: 35.6%

IR $\nu$ max KBr(cm$^{-1}$) 1742, 1650, 1634, 1540, 1532, 1504

NMR (D$_2$O) $\delta$ 8.50(2H, d), 7.22(2H, d), 6.68(1H, s), 5.21(1H, d), 4.13(3H, s), 3.78(3H, s)

EXAMPLE 8

Preparation of (6R, 7S)-7-[2-(2-aminothiazol-4-yl)-2-syn-methoxyimino-acetamido]-3-(2-aminothiazol-4-yl-methylthio)-1-azabicyclo [4.2.0]-oct-2-en-8-oxo-2-carboxylic acid The same procedure as in Example 1 was repeated except that 0.12 ml of 2-amino-4-mercaptomethyl-thiazol was used in place of the 4-mercaptomethylpyridine used in Example 1, whereby 62 mg of a white powder was obtained. The powder had the following physical properties and was identified to be the captioned compound.

Yield: 54%

IR ν max KBr(cm$^{-1}$) 1750, 1742, 1670, 1654, 1620, 1540

NMR(DMSO-d$_6$+CD$_3$OD) δ 6.77(1H, s), 6.33 (1H, s), 5.40(1H, d), 3.87(3H, s), 2.6(2H, m), 2.1–1.8(2H, m)

EXAMPLE 9

Preparation of (6R, 7S)-7-[2-(2-aminothiazol-4-yl)-2-syn-methoxyimino-acetamido]-3-(1-carbamoylmethyl-pyridinium-4-yl-methylthio)-1-azabicyclo [4.2.0]-oct-2-en-8-oxo-2-carboxylate At first, 200 mg of benzhydryl ester of (6R, 7S)-7-[2-(2-tritylaminothiazol-4-yl)-2-syn-methoxyimino-acetamido]-3-(4-pyridylmethylthio)-1-azabicyclo [4.2.0]-oct-2-en-8-oxo-2-carboxylic acid was dissolved in 5 ml of methylene chloride, and 120 mg of acetamide iodide was added thereto. The mixture was subjected to reaction for 2 days. The reaction mixture was concentrated under reduced pressure, and 2 ml of methylene chloride, 0.2 ml of anisole and 2 ml of trifluoroacetic acid were added to the residue. The mixture was subjected to reaction at room temperature for 2 hours. The reaction mixture was concentrated, and 4 ml of methanol and 0.4 ml of water were added to the residue. After having been adjusted to pH 1, the mixture was stirred for 2 hours. The reaction mixture was concentrated, and the resulting brown oily matter was purified by column chromatography using 40 ml of Diaion HP-10 (eluting agent; water:methanol=2:1), whereby 79 mg of a light brown powder was obtained. The powder had the following physical properties and was identified to be the captioned compound.

Yield: 65.7%

IR ν max KBr(cm$^{-1}$) 1747, 1692, 1659, 1642, 1592, 1544, 1529

NMR (D$_2$O) δ 8.63(2H, d), 7.96(2H, d), 6.82(1H, s), 5.40(2H, s), 3.92(3H, s), 2.5–1.3(4H, m)

EXAMPLE 10

Preparation of (6R, 7S)-7-[2-(2-aminothiazol-4-yl)-2-syn-methoxyimino-acetamido]-3-(N-methylimidazol-2-ylmethyl) thio-1-azabicyclo [4.2.0]-oct-2-en-8-oxo-2-carboxylic acid At first, 0.348 ml of diisopropylethylamine and then 331 mg of 2-mercaptomethyl-N-methylimidazol were added to a solution of 1.26g of benzhydryl ester of (6R, 7S)-7-[2-(2-tritylamino-thiazol-4-yl)-2-syn-methoxyimino-acetamido]-3-methanesulfonyloxy-1-azabicyclo [4.2.0]-oct-2-en-8-oxo-2-carboxylic acid in 13 ml of DMF at 0° C. with stirring. The reaction mixture was stirred at room temperature for 5 hours, and then DMF was removed therefrom by distillation under reduced pressure. Chloroform and water were added thereto, and the organic layer was separated therefrom. The aqueous layer was adjusted to pH 7.2 and extracted three times with chloroform. The organic layers were joined together, and the mixture was washed with an aqueous saturated sodium bicarbonate solution, and then with an aqueous saturated sodium chloride solution, and dried over anhydrous magnesium sulfate. The solvent was removed therefrom by distillation under reduced pressure. The resulting crude product was subjected to separation and purification by silica gel column chromatography (1% methanol/chloroform), whereby 1.31 g of benzhydryl ester of (6R, 7S)-7-[2-(2-tritylaminothiazol-4-yl)-2-syn-methoxyiminoacetamido]-3-(N-methyl-imidazol-2-ylmethyl) thio-1-azabicyclo [4.2.0]-oct-2-en-8-oxo-2-carboxylic acid was obtained.

Yield: 100%

Then, 3 ml of anhydrous methylene chloride and 0.2 ml of anisol were added to 305 mg of the thus obtained adduct, and 3 ml of trifluoroacetic acid was added thereto at 0° C. The mixture was stirred at 0° C. for 15 minutes, and the solvent was removed therefrom by distillation under reduced pressure. Then, 4.5 ml of methanol and 0.5 ml of water were added thereto, and the mixture was stirred at 50° C. for one hour. The solvent was removed therefrom by distillation under reduced pressure, and the residue was purified by Diaion HP-10 (10 ml; 25% methanol/water), whereby 102 mg of the captioned compound was obtained as a light yellow powder. The powder had the following physical properties and was identified to be the captioned compound.

IR ν max KBr(cm$^{-1}$) 1746(vs), 1652(m), 1646(sh), 1590, 1539

NMR(DMSO-d$_6$) δ 9.25 (1H, d, J=8.4 Hz), 7.3–7.0 (2H, m), 7.19(1H, br. s), 6.93(1H, s), 6.70(1H, s) 5.40(1H, dd, J=5.4, 8.4 Hz), 4.18(2H, d, J=11.5 Hz), 4.0–3.5(1H,m), 3.82(3H, s), 3.60(3H, s), 2.8–2.2(2H, m) 2.1–1.1(2H, m)

EXAMPLE 11

Preparation of (6R, 7S)-7-[2-(2-aminothiazol-4-yl)-2-syn-methoxyimino-acetamido]-3-(N,N'-dimethylimidazolium-2-ylmethyl) thio-1-azabicyclo [4.2.0]-oct-2-en-8-oxo-2-carboxylate At first, 200 mg of benzhydryl ester of (6R, 7S)-7-[2-(2-tritylaminothiazol-4-yl)-2-syn-methoxyimino-acetamido]-3-(N-methylimidazol-2-ylmethyl) thio-1-azabicyclo [4.2.0]-oct-2-en-8-oxo-2-carboxylic acid obtained in Example 10 was dissolved in 2 ml of methylene chloride, and 2 ml of methyl iodide was added thereto. The mixture was stirred for 2 days, and the solvent was removed therefrom by distillation under reduced pressure. The residue was subjected to the same conditions for removing the protective group as in Example 10. The resulting residue was subjected to separation and purification using Diaion HP-10 (10 ml: 15% methanol/water), and, after freeze-drying, 56.2 mg of the captioned compound was obtained as a white powder.

Yield: 54%

IR ν max KBr(cm$^{-1}$) 1748, 1700, 1655, 1612, 1545, 1538

NMR (D$_2$O) 7.40(2H, s), 6.99(1H, s), 5.47(1H, d, J=5.1 Hz), 4.35(2H, br. s) 4.2–3.8(1H, m), 4.02(3H, s), 3.88(6H, s), 2.7–1.5(4H,m)

EXAMPLE 12

Preparation of (6R, 7S)-7-[2-(2-aminothiazol-4-yl)-2-syn-methoxyimino-acetamido]-3-(2,4-dimethylthiazol- 5-ylmethyl) thio-1-azabicyclo [4.2.0]-oct-2-en-8-oxo-2-carboxylic acid The same procedure as in Example 1 was repeated, except that 2,4-dimethyl-5-mercaptomethylthiazol was used in place of the 4-mercaptomethylpyridine used in Example 1, whereby 75.8 mg(30%) of a white powder was obtained. The powder had the following physical properties and was identified to be the captioned compound.

IR ν max KBr(cm$^{-1}$) 1756, 1655, 1530

NMR(DMSO-d$_6$) δ 9.28(1H, d, J=8.8 Hz) 7.20(2H, br, s), 6.76(1H, s), 5.39(1H, dd, J=4.4, 8.8 Hz), 4.22(2H, br. s), 4.0–3.7 (1H, m), 3.84(3H, s), 2.51(3H, s), 2.3–1.6(4H, m), 2.26(3H, s), 1.4–1.1(2H,m)

EXAMPLE 13

Preparation of 7-(D-phenylglycylamido)-3-(4-pyridylmethylthio)-3-cephem-4-carboxylic acid 1) Synthesis of diphenylmethyl 7-[(R)-2-phenyl-2-t-butoxycarbonylamino) acetamido]-3-(4-pyridyl) methylthio-3-cephem-4-carboxylate At first, 633.5 mg of diphenylmethyl 7-[((R)-2-phenyl-2-t-butoxycarbonylamino) acetamido]-3-chloro-3-cephem-4-carboxylate was dissolved in 5 ml of anhydrous dimethylformamide, and 250 mg of (4-pyridyl) methylthiol and 416 mg of sodium hydrogen sulfite were added thereto. The mixture was subjected to reaction at room temperature for 3 hours, and then 104 mg of sodium hydrogen sulfite was added thereto. The mixture was subjected to reaction for 2 hours. Then, 10 ml of water was added to the reaction mixture, and the mixture was extracted three times with ethyl acetate. The organic layers were joined together, and the mixture was washed with water and then with an aqueous saturated sodium chloride solution, dried over anhydrous sodium sulfate and concentrated under reduced pressure. The residue was subjected to silica gel chromatography and fractions eluted with n-hexane-ethyl acetate (½) were joined together, whereby 480 mg of the captioned compound was obtained.

Yield: 66.5%

IR ν max KBr(cm$^{-1}$) 2980, 1784, 1672, 1602, 1496, 1454, 1368

NMR (CDCl$_3$+CD$_3$OD$_3$) δ 8.5–8.35(2H, m), 7.5 7.3(5H, m), 7.2–7.1(2H, m), 6.93(1H, s), 5.66(1H, d, J=5.1 Hz), 5.23(1H, s), 4.87(1H, d, J=5.1 Hz), 3.8(2H, s), 3.32(2H, s)

2) Synthesis of 7-(D-phenylglycylamido)-3-(4-pyridyl) methylthio-3-cephem-4-carboxylate At first, 250 mg of diphenylmethyl 7-[((R)-2-phenyl-2-t-butoxycarbonylamino) acetamido-3-(4-pyridyl) methylthio-3-cephem-4-carboxylate was dissolved in 4 ml of anhydrous methylene chloride and 0.1 ml of anisole, and 4 ml of trifluoroacetic acid cooled to 0° C. in advance was added thereto. The mixture was subjected to reaction at 0° C. for 90 minutes. Then, 30 ml of toluene was added thereto, and the mixture was concentrated under reduced pressure, and an appropriate amount of water was added to the residue. The mixture was adjusted to pH 4.5–5.0 with sodium hydrogen carbonate. The mixture was passed through a column of Diaion HP-10, and the fractions eluted with an aqueous 50% methanol solution were joined together, whereby 150 mg of the captioned compound was obtained.

Yield 95%

IR ν max KBr(cm$^{-1}$) 3406, 1766, 1689, 1603, 1506, 1391, 1342, 1251, 1181

NMR(CD$_3$OD+D$_2$O+DCl+DMSO-d$_6$) δ 8.87(2H, d, J=6.3 Hz), 8.07(2H, d, J=6.3 Hz), 7.63(5H, s), 5.73(1H, d, J=5.1 Hz), 5.33(1H, s), 5.20(1H, d, J=5.1 Hz), 4.41 (2H, s), 3.80(1H, d, J=18 Hz), 3.60(1H, d, J=18 Hz)

EXAMPLE 14

Preparation of 7-(D-phenylglycylamido)-3-(4-methylpyridiniummethylthio)-3-cephem-4-carboxylic acid trifluoroacetate 1) Synthesis of diphenylmethyl 7-[((R)-2-phenyl-t-butoxycarbonylamino) acetamido]-3-(4-methylpyridinium) methylthio-3-cephem-4-carboxylate iodide At first, 220 mg of diphenylmethyl 7-[((R)-2-phenyl-2-t-butoxycarbonylamino) acetamido]-3-(4-pyridyl) methylthio-3-cephem-4-carboxylate was dissolved in 5 ml of anhydrous methylene chloride, and 0.2 ml of methyl iodide was added thereto. The mixture was subjected to reaction overnight, and then concentrated under reduced pressure, whereby the captioned compound was obtained.

IR ν max KBr(cm$^{-1}$) 3182, 2978, 1780, 1672, 1645, 1557, 1509, 1496

NMR(CDCl$_3$+CD$_3$OD) δ 8.60(2H, d, J=6.0 Hz), 7.70(2H, d, J=6.0 Hz), 7.6–7.2(5H,m), 6.81(1H, s), 5.65(1H, d, J=5.1 Hz), 5.27(1H, s), 5.08(1H, d, J=5.1 Hz), 4.43(3H, s), 4.29(2H, s), 4.22–4.08(1H,m), 3.75–3.65(1H, m), 1.45(9H, s)

2) Synthesis of 7-(D-phenylglycylamido)-3-(4-methylpyridinium) methylthio-3-cephem-4-carboxylic acid trifluoroacetate At first, 220 mg of diphenylmethyl 7-[((R)-2-phenyl-2-t-butoxycarbonylamino) acetamido]-3-(4-methylpyridinium) methylthio-3-cephem-4-carboxylate iodide was dissolved in 4 ml of anhydrous methylene chloride and 0.2 ml of anisole, and 4 ml of trifluoroacetic acid precooled to 0° C. was added thereto. The mixture was subjected to reaction at 0° C. for 40 minutes. Then, 10 ml of toluene was added thereto, and the mixture was concentrated under reduced pressure. The residue was dissolved in a small amount of water and the mixture was adjusted to pH 4.5 with sodium hydrogen carbonate, and passed through a column of Diaion HP-10. The fractions eluted with an aqueous 50% methanol solution were joined together, whereby 74 mg of the captioned compound was obtained.

IR ν max KBr(cm$^{-1}$) 1788, 1713, 1508, 1468, 1455, 1383, 1332, 1271, 1222

NMR (D$_2$O) δ 8.60(2H, d, J=6.7 Hz), 7.86(2H, d, J=6.7 Hz), 7.53(5H, s), 5.67(1H, d, J=4.6 Hz), 5.18(1H, s), 5.04(1H, d, J=4.6 Hz), 4.31(3H, s), 4.11(2H, s), 3.65(1H, d, J=17.2 Hz), 3.31(1H, d, J=17.2 Hz)

EXAMPLE 15

Preparation of 7-[2-(2-aminothiazol-4-yl)-2-syn-methoxyimino] acetamido-3-(4-pyridylmethylthio)-3-cephem-4-carboxylic acid 1) Preparation of diphenylmethyl
7-[2-(2-tritylaminothiazol-4-yl)-2-syn-methoxyimino]
acetamido-3-(4-pyridyl)
methylthio-3-cephem-4-carboxylate At first, 1.4g of diphenylmethyl 7-[2-(2-tritylaminothiazol-4-yl)-2-syn-methoxyimino] acetamido-3-chloro-3-cephem-4-carboxylate was dissolved in 5 ml of anhydrous dimethylformamide and 4 equivalent weights of sodium bisulfite was added thereto. Then, 500 ml of (4-pyridyl) methylthiol was added thereto, and the mixture was stirred at room temperature for 4 hours. Then, 10 ml of water and 2 ml of an aqueous saturated sodium hydrogen carbonate solution were added thereto, and the mixture was extracted three times with ethyl acetate. The organic layers were joined together, and the mixture was washed twice with an aqueous saturated sodium chloride solution, dried over anhydrous sodium sulfate, and concentrated under reduced pressure. The residue was subjected to silica gel column chromatography and the fractions eluted with n-hexane-ethyl acetate [⅛(V/V)] were joined together, whereby 980 mg of the captioned compound was obtained.

IR $\nu$ max KBr(cm$^{-1}$) 1784, 1731, 1672, 1599, 1561, 1523, 1496, 1449, 1415

NMR(CDCl$_3$+CD$_3$OD) $\delta$ 8.45–8.2(2H, m), 7.31(25H, m), 6.92(1H, s), 7.70(1H, s), 5.71(1H, d, J=4.9 Hz), 5.03(1H, d, J=4.9 Hz), 3.97(3H, s), 3.91(2H, s), 3.50(2H, s)

2) Preparation of
7-[2-(2-aminothiazol-4-yl)-2-syn-methoxyimino]
acetamido-3-(4-pyridyl)
methylthio-3-cephem-4-carboxylic acid At first, 90 mg of diphenylmethyl 7-[2-(2-tritylaminothiazol-4-yl)-2-syn-methoxyimino]acetamido-3-(4-pyridyl) methylthio-3-cephem-4-carboxylate was dissolved in one ml of anhydrous methylene chloride, and 0.2 ml of anisole was added thereto with ice cooling. Furthermore, one ml of trifluoroacetic acid cooled to 0° C. in advance was added thereto, and the mixture was subjected to reaction at 0° C. for one hour. Then, the reaction mixture was concentrated under reduced pressure, and the residue was dissolved in water. The solution was adjusted to pH 2.0 with sodium hydrogen carbonate and then passed through a column of Diaion HP-10. The fractions eluted with an aqueous 50% methanol solution were joined together, whereby 22 mg of the captioned compound was obtained.

IR $\nu$ max KBr(cm$^{-1}$) 3400, 1770, 1705, 1664, 1655, 1648, 1637, 1603, 1561, 1540, 1507, 1385

NMR(CD$_3$OD+D$_2$O) $\delta$ 8.63(2H, d, J=5.6 Hz), 7.84(2H, d, J=5.6 Hz), 6.89(1H, s), 5.75(1H, d, J=4.9 Hz), 4.17(2H, s), 4.00(3H, s), 3.73(1H, d, J=18.3 Hz), 3.43(1H, d, J=18.3 Hz)

EXAMPLE 16

Preparation of
7-[2-(2-aminothiazol-4-yl)-2-syn-methoxyimino]
acetamido-3-(1-methylpyridinium-4-yl)methylthio-
3-cephem-4-carboxylate 1) Preparation of diphenylmethyl
7-[2-(2-tritylaminothiazol-4-yl)-2-syn-methoxyimino]
acetamido-3-(1-methylpyridinium-4-yl)
methylthio-3-cephem-4-carboxylate iodide At fist, 270 mg of diphenylmethyl 7-[2-(2-tritylaminothiazol-4-yl)-2-syn-methoxyimino] acetamido-3-(4-pyridye) methylthio-3-cephem-4-carboxylate was dissolved in 5 ml of anhydrous methylene chloride, and 0.1 ml of methyl iodate was added thereto. The mixture was left standing for 3 days, and concentrated under reduced pressure, whereby 333 mg of the captioned compound was obtained.

IR $\nu$ max KBr(cm$^{-1}$) 1764, 1664, 1639, 1518

2) Preparation of
7-[2-(2-aminothiazol-4-yl)-2-syn-methoxyimino]
acetamido-3-(1-methylpyridinium-4-yl)
methylthio-3-cephem-4-carboxylate At first, 300 mg of diphenylmethyl 7-[2-(2-tritylaminothiazol-4-yl)-2-syn-methoxyimino] acetamido-3-(1-methylpyridinium-4-yl) methylthio-3-cephem-4-carboxylate iodide was dissolved in 3 ml of anhydrous methylene chloride, and 0.2 ml of anisole was added thereto. Then, 3 ml of trifluoroacetic acid cooled to 0° C. in advance was added thereto with ice cooling and stirring, and the mixture was subjected to reaction for 30 minutes. Then, 5 ml of toluene was added thereto, and the mixture was concentrated under reduced pressure. The residue was washed with ether, and dissolved in a small amount of water-dimethyl sulfoxide [1:1(v/v)]. The solution was adjusted to pH 2.5 with sodium hydrogen carbonate, and then passed through a column of Diaion HP-10. Then, the fractions eluted with an aqueous 50% methanol solution were joined together, whereby 78 mg of the captioned compound was obtained.

IR $\nu$ max KBr(cm$^{-1}$) 3400, 3272, 1764, 1654, 1636, 1608, 1531, 1468, 1389, 1346

NMR(CD$_3$OD) $\delta$ 8.70(2H, d, J=6.8 Hz), 7.94(2H, d, J=6.8 Hz), 6.93(1H, s), 5.74(1H, d, J=4.9 Hz), 5.16(1H, d, J=4.9 Hz), 4.35(3H, s), 4.17(2H, s), 4.00(3H, s), 3.79(1H, d, J=17.1 Hz), 3.48(1H, d, J=17.1 Hz)

EXAMPLE 17

Preparation of (6R, 7S)-7-[2-(2-aminothiazol-4-yl)-2-syn-methoxyiminoacetamido]-3-(1,2,3-thiadiazol-4-ylmethyl) thio-1-azabicyclo [4.2.0]-oct-2-en-8-oxo-2-carboxylic acid The same procedure as in Example 1 was repeated except that 4-mercaptomethyl-1,2,3-thiadiazol was used in place of the 4-mercaptomethylpyridine used in Example 1, whereby 163 mg of a white powder was obtained. The powder had the following physical properties and was identified to be the captioned compound.

Yield 74%

IR $\nu$ max KBr(cm$^{-1}$) 1740, 1682,1654, 1531

NMR(DMSO-d$_6$) $\delta$ 9.25(1H, d, J=9.3 Hz) 9.04(1H, s), 7.16(2H, br. s), 6.77(1H, s), 5.43(1H, dd, J=5.8, 9.3 Hz), 4.56(2H, br. s), 4.0–3.71(1H, m) 3.86(3H, s), 2.9–1.2(4H, m)

EXAMPLE 18

In this example, 200g of the white powder obtained in the same manner as in Example 1 is dissolved in 5 l of water for injection, and the solution is subjected to pressure filtration (2 kg/cm$^2$) with N$_2$ gas using BTS membrane having a pore size of 0.1$\mu$ and diameter of 142 mm (available from Branzuick Co.). The filtrate is dried by a sanitary spray dryer to obtain a sterile powder having a diameter of 50$\mu$ or less. The, 200 mg portions of the sterile powder are put in 5 ml-sterile glass vials, and sterile rubber stoppers are applied thereto, whereby preparations for injection are prepared. When used, the preparation is dissolved in water for injection and administered to a patient.

EXAMPLE 19

In this example, one ml portions of the filtrate obtained by treating the yellow powder obtained in Example 2 in the same manner as in Example 18 are poured into 5 ml-sterile glass vials and freezed at −45° C. Then, primary drying is conducted at 20° C. under 0.05 mbar for 20 hours and secondary drying, at 30°–40° C. for 20 hours. The thus obtained freeze-dried product is a white powder and has water content of 2% or less. The freeze-dried product is treated in the same manner as in the treatment of "the sterile powder" in Example 18 to obtain a preparation for injection.

REFERENCE EXAMPLE 1

Synthesis of diphenylmethyl 7-[((R)-2-phenyl-2-t-butoxycarbonylamino) acetamido]-3-chloro-3-cephem-4-carboxylate At first, 1.0g of 7-(D-phenylglycylamido)-3-chloro-3-cephem-4-carboxylic acid was suspended in 30 ml of tetrahydrofuran and 20 ml of water, and triethylamine was added thereto with ice cooling and stirring to adjust the suspension to pH 8.5 and make a solution. Then, 2.38g of di-t-butyl dicarbonate was added to the solution, and the mixture was stirred with ice cooling for 2 hours. Then, 1.19g of di-t-butyl dicarbonate was added thereto, and the mixture was subjected to reaction for one hour. During the reaction, the pH of the reaction mixture was kept at 7.8-8.2 by adding triethylamine thereto. Then, the pH of the reaction mixture was adjusted to 2.2 with 1N hydrochloric acid, and the mixture was extracted three times with ethyl acetate. The organic layers were joined together, and the mixture was washed with water and then with an aqueous saturated sodium chloride solution, dried over anhydrous sodium sulfate, and concentrated under reduced pressure. The residue was washed with n-hexane-ethyl acetate (1:1) and dissolved in 30 ml of anhydrous methylene chloride. Diphenyldiazomethane was added thereto, and at the time when the color of mixture did not return to red despite the addition of diphenyldiazomethane, the mixture was subjected to concentration under reduced pressure. The residue was washed five times with n-hexane and subjected to silica gel column chromatography in a development system of n-hexane-ethyl acetate [1/1(v/v)], whereby 1.23 g of the captioned compound was obtained.

Yield 71.3%

IR ν max KBr(cm$^{-1}$) 3320, 1783, 1721, 1687, 1665, 1615, 1559, 1519, 1497

NMR(CDCl$_3$+CD$_3$OD) δ 7.5-7.2(5H, m), 6.93(1H, s), 5.75(1H, d, J=4.5 Hz), 5.23(1H, s), 4.96(1H, d, J=4.5 Hz), 3.71(1H, d, J=18 Hz), 3.36(1H, d, J=18 Hz)

REFERENCE EXAMPLE 2

Synthesis of diphenylmethyl 7-[2-(2-tritylaminothiazol-4-yl)-2-syn-methoxyimino] acetamido-3-chloro-3-cephem-4-carboxylate At first, 960 mg of 7-amino-3-chloro-3-cephem-4-carboxylic acid was dissolved in 350 ml of 1/15M phosphate buffer (pH 7.38) and 120 ml of tetrahydrofuran, and the solution was stirred with ice cooling. Separately, 2.17 g of 2-(2-tritylaminothiazol-4-yl)-2-syn-methoxyiminoacetic acid was dissolved in 50 ml of anhydrous tetrahydrofuran, and 0.68 ml of triethylamine was added thereto at under cooling at −70° C. And then 1.02 g of phosphorus pentachloride was added thereto. The temperature of the mixture was slowly raised from −30° C. to 0° C. with stirring to prepare an acid chloride solution. The thus obtained acid chloride solution was dropwise added to the amino acid solution while adding triethylamine thereto to keep pH 7.4–8.0. After the dropwise addition, the mixture was stirred for 30 minutes, adjusted to pH 2.0 with 1N hydrochloric acid and saturated with sodium chloride. Then, the mixture was extracted three times with ethyl acetate, and the organic layers were joined together. The mixture was washed with water, and then with an aqueous saturated sodium chloride solution, dried over anhydrous sodium sulfate and concentrated under reduced pressure. The residue was dissolved in 100 ml of methylene chloride, and diphenyldiazomethane was added thereto until the color of solution did not return to red. Then, the mixture was concentrated under reduced pressure. The residue was washed five times with n-hexane, subjected to silica gel column chromatography and eluted with n-hexane-ethylacetate [2/1(v/v)], whereby 2.7 g of the captioned compound was obtained.

Yield: 79.9%

IR ν max KBr(cm$^{-1}$) 3062, 3034, 1788, 1732, 1682, 1599, 1522, 1495, 1448

NMR(CDCl$_3$+CD$_3$OD) δ 7.31(15H, m), 6.95(1H, s), 6.66(1H, s), 5.81(1H, d, J=5.2 Hz), 5.14(1H, d, J=5.2 Hz), 3.98(3H, s), 3.73(1H, s), 3.58(1H, s)

REFERENCE EXAMPLE 3

Preparation of benzhydryl ester of (6R, 7S)-7-[2-(2-tritylaminothiazol-4-yl)-2-syn-methoxyiminoacetamido-3-methanesulfonyloxy-1-azabicyclo [4.2.0]-oct-2-en-8-oxo-2-carboxylic acid At first, 2.0 g of (±)cis 7-β-amino-3-methanesulfonyloxy-1-azabicyclo [4.2.0]-oct-2-en-8-oxo-2-carboxylic acid was added to 50 ml of tetrahydrofuran and 50 ml of water, and dissolved therein by adjusting the mixture to pH 7.5 with an aqueous saturated sodium hydrogen carbonate solution. Then, 1.5 ml of phenylacetyl chloride was dropwise added to the solution with stirring while keeping the pH at 7 with an aqueous saturated sodium hydrogen carbonate solution. After reaction at room temperature for one hour, 20 ml of ethyl acetate was added to the reaction mixture, and the organic layer was separated and removed therefrom. The aqueous layer was adjusted to pH 1.9 and extracted twice with 50 ml of ethyl acetate. The solvent was removed from the extracts by distillation, whereby light yellow granula crystals were obtained. The crystals were dissolved in 100 ml of phosphate buffer (pH 6.5), and 100 ml of immobilized enzyme having a penicillin acylase activity [whose preparation is disclosed in Japanese Published Unexamined patent application No. 138396/1980 and EPO 014476Al]was added thereto. The mixture was shaked at 30° C. for 4.5 hours while adjusting the pH to 7.0 with 1N cerium hydroxide. The immobilized enzyme was removed therefrom by filtration, and the filtrate was adjusted to pH 1.9 and washed twice with 50 ml of ethyl acetate. The aqueous layer was adjusted to pH 3.0 and then concentrated to about one half of the volume. The deposited crystals were recovered by filtration and dried, whereby 0.66g of (6R, 7S)-7-amino-3-methanesulfonyloxy-1-azabicyclo [4.2.0]-oct-2-en-8-oxo-2-carboxylic acid was obtained. The thus obtained crystals were added to 20 ml of water and 20 ml of tetrahydrofuran, and the mixture was adjusted to pH 7.0 with an aqueous sodium hydrogen carbonate solution to make a solution. An acid chloride solution obtained by stirring 0.76 g of 2-tritylamino-2-syn-methoxyiminoacetic acid, 0.37 g of phosphorus pentachloride and 0.25 ml of triethylamine in 10 ml of tetrahydrofuran at −20° C. was dropwise added thereto while keeping the pH at 7.0. After the dropwise addition, the mixture was subjected to reaction with ice cooling for one hour. Then, the pH of the reaction mixture was adjusted to 2, and the mixture was extracted twice with 50 ml of ethyl acetate. The solvent was removed from the extracts by distillation, and 30 ml of chloroform was added to the residue. Then, 0.5 g of diphenyldiazomethane was added to the resulting solution to cary out esterification, and the reaction mixture was concentrated. The residue was purified by column chromatography using 100 ml of silica gel (eluting agent; chloroform; ethyl acetate=20:1), whereby 0.73 g of the captioned compound was obtained as a light yellow powder.

NMR(CDCl$_3$+CD$_3$OD) δ 7.28(25H, s), 6.87(1H, s), 6.54(1H, s), 5.48(1H, d), 3.96(3H, s), 3.8(1H,m), 2.87(3H, s)

REFERENCE EXAMPLE 4

Antibacterial activities (MIC μg/ml) of the compounds of the present invention on Mueller-Hinton agar (pH 7.2) according to the dilution method are shown in Table 1, where a test compound is represented by Example number under which the preparation of the compound is described.

TABLE 1

| Example No. | Staphylococcus aureus 209-P | Staphylococcus epidermidis F-1 | Escherichia coli NIHJ JC-2 | Krebsiella pneumoniae KY8645 |
|---|---|---|---|---|
| 1 | 0.78 | 3.13 | 0.01 | 0.05 |
| 2 | 0.39 | 1.56 | 0.1 | 0.1 |
| 3 | 1.56 | 3.13 | 0.02 | 0.05 |
| 4 | 0.78 | 6.25 | 0.02 | 0.05 |
| 5 | 0.1 | 0.39 | 12.5 | 12.5 |
| 6 | 0.78 | 6.25 | 0.02 | 0.1 |
| 7 | 0.78 | 3.13 | 0.1 | 0.1 |
| 13 | 0.39 | 3.13 | 6.25 | 3.13 |
| 15 | 0.39 | 3.13 | 0.05 | 0.1 |

What is claimed is:

1. A carbacephem compound represented by the formula:

R$_2$CONH—[β-lactam fused ring]—S(CH$_2$)$_n$R$_1$, CO$_2$R$_3$ wherein:

n is an integer of from 1 to 5;
R$_1$ is an unsubstituted or substituted pyridyl group wherein the substituent is an alkyl group having 1 to 6 carbon atoms or —(CH$_2$)$_m$Y group, wherein Y is a carbamoyl group, and m is an integer of 1 to 5;
R$_2$ is a group represented by the formula:

$$R_4-\underset{NH_2}{\underset{|}{CH}}-$$

wherein R$_4$ is a phenyl group optically substituted with an alkyl group having 1 to 6 carbon atoms, hydroxyl, amino, nitro or carboxyl group, or a group represented by the formula:

[thiazole ring with H$_2$N— and =N—OR$_5$]

wherein R$_5$ is an alkyl group having 1 to 7 carbon atoms optionally substituted with a hydroxyl, carboxyl or sulfo group;
R$_3$ is hydrogen, an alkali metal, an alkaline earth metal, an ammonium group of a basic amino acid, or an ester represented by the formula:

$$-\underset{R_6}{\underset{|}{CH}}-O\overset{O}{\overset{\|}{C}}-R_7$$

wherein R$_6$ is hydrogen or an alkyl group having 1 to 6 carbon atoms, and R$_9$ is an alkyl group having 1 to 6 carbon atoms or phenyl group, or a group represented by the formula:

[phthalide group =O]

and R$_1$ may be quarternary ammonium group where —CO$_2$R$_3$ represents —CO$_2^-$.

2. An antibacterial pharmaceutical composition comprising, as an active ingredient, an effective amount of a compound of claim 1 in association with a pharmaceutical carrier or diluent.

* * * * *

UNITED STATES PATENT AND TRADEMARK OFFICE
CERTIFICATE OF CORRECTION

PATENT NO. : 4,760,060

DATED : July 26, 1988

INVENTOR(S) : KENICHI MOCHIDA, ET AL.

It is certified that error appears in the above-identified patent and that said Letters Patent is hereby corrected as shown below:

Column 8, line 28, "NMR($CD_3OD$)" should read --NMR($CD_3OD$)--;

Column 18, line 13, "optically" should read --optionally--;

line 39, "$R_9$" should read --$R_7$--;

line 51, "quarternary" should read --quaternary--.

Signed and Sealed this

Twenty-fourth Day of January, 1989

Attest:

DONALD J. QUIGG

*Attesting Officer*     Commissioner of Patents and Trademarks